(12) United States Patent
Twydell et al.

(10) Patent No.: US 9,700,039 B2
(45) Date of Patent: Jul. 11, 2017

(54) RODENTICIDAL SOFT BAIT COMPOSITION

(71) Applicant: BASF Agro B.V., Arnhem (NL)

(72) Inventors: Roland Stephen Twydell, Chester (GB); Sharon Hughes, Widnes (GB); Holger Dutzig, Rheinzabern (DE)

(73) Assignee: BASF Agro B.V., Arnheim (NL)

( * ) Notice: Subject to any disclaimer, the term of this patent is extended or adjusted under 35 U.S.C. 154(b) by 0 days.

(21) Appl. No.: 14/779,149

(22) PCT Filed: Mar. 24, 2014

(86) PCT No.: PCT/EP2014/055816
§ 371 (c)(1),
(2) Date: Sep. 22, 2015

(87) PCT Pub. No.: WO2014/154621
PCT Pub. Date: Oct. 2, 2014

(65) Prior Publication Data
US 2016/0050910 A1    Feb. 25, 2016

(30) Foreign Application Priority Data
Mar. 27, 2013 (EP) .................. 13161244

(51) Int. Cl.
*A01N 25/08* (2006.01)
*A01N 25/00* (2006.01)
*A01N 31/06* (2006.01)

(52) U.S. Cl.
CPC ........... *A01N 25/004* (2013.01); *A01N 31/06* (2013.01)

(58) Field of Classification Search
CPC .................................. A01N 25/004
See application file for complete search history.

(56) References Cited

U.S. PATENT DOCUMENTS

2006/0222676 A1* 10/2006 Zambotto ............ A01N 25/004
424/410
2008/0317801 A1* 12/2008 Hughes ............... A01N 25/004
424/408

FOREIGN PATENT DOCUMENTS

| DE | 198 37 064 | 2/2000 |
| EP | 2 497 362 | 9/2012 |
| WO | WO 2004/098286 | 11/2004 |
| WO | WO 2014064272 | 5/2014 |

OTHER PUBLICATIONS

European Search Report, dated Jul. 15, 2013, prepared in EP Application No. 13 16 1244.
International Preliminary Report on Patentability dated Jun. 10, 2015, prepared in International Application No. PCT/EP2014/055816.
International Search Report dated Apr. 8, 2014, prepared in International Application No. PCT/EP2014/055816.

* cited by examiner

*Primary Examiner* — Theodore R West
(74) *Attorney, Agent, or Firm* — Brinks Gilson & Lione

(57) ABSTRACT

Rodenticidal soft bait compositions are provided which consist of a mixture, in the form of a paste, comprising vegetable flour, a fat which is not completely liquid at a temperature of 35° C. and at least one rodenticidally-active substance. The vegetable flour is present in the mixture in an amount of at least 60%, preferably 62 to 78%, by weight based on the total weight of the mixture. The weight ratio of the vegetable flour to fat in the mixture is 4:1 to 8:1, preferably 5:1 to 7.5:1. The soft bait compositions are extremely palatable to rodents such that rodents are encouraged to consume a sufficient amount to deliver a lethal dose of rodenticide in a single sitting. Also provided is a method for manufacturing the soft bait composition of the invention.

27 Claims, No Drawings

RODENTICIDAL SOFT BAIT COMPOSITION

This application is a National Stage application of International Application No. PCT/EP2014/055816 filed Mar. 24, 2014. This application also claims priority under 35 U.S.C. §119 to European Patent Application No. 13161244.2 filed Mar. 27, 2013.

The present invention relates to a rodenticidal soft bait composition, to a method of manufacturing this and to its use in the control of rodents, particularly rats and mice.

Rodent populations, especially those of rats and mice, are controlled principally because of the economic damage they cause. Rats and mice are responsible for large scale food/feed consumption and spoilage and cause structural damage to buildings and other damage resulting from their habits of chewing and digging. Infestations by rats and mice are often controlled by the administration of poison formulations. Bait blocks are often used to avoid the scattering of poisoned bait and because they are generally more resistant to damp or wet conditions.

Rodenticidal block baits have traditionally been manufactured by dispersing feed materials and one or more rodenticides in a hard or semi-solid wax, typically paraffin wax, binder. The mixture is then moulded or formed into suitably sized and shaped blocks which can be placed in a location close to signs of rodent activity but inaccessible to children and non-target animals or in tamper-proof bait stations.

Unfortunately, rodenticidal wax block baits are considered to have poor palatability characteristics for rodents.

To be useful as a bait, a composition needs to be attractive and palatable to the target rodent.

Certain rodenticidally-active substances have an antifeedant effect on rodents that have consumed them. Such substances, when consumed, have an effect of inhibiting the normal feeding behaviour of the rodent. It is critical, therefore, that a bait is sufficiently palatable to the rodent to encourage the rodent to consume more of the bait despite the antifeedant effect brought about by the consumption of the active substance and, thus, take a lethal dose of the bait in one sitting.

It is well known that the natural behaviour of rats and mice is to forage or scavenge for food. Typically, a rat will take a small amount of food from a food source and then look for something different to eat. It is common to use, in a bait, a rodentically-active substance which takes effect within a short time after consumption. If a rat experiences any feelings of sickness or discomfort after eating, it remembers the source of the food consumed and subsequently avoids that source. Since there may be only a short time from when a rat eats from a bait to when it begins to suffer, it is necessary to make the bait very palatable so that the rat will eat a sufficient amount of this to deliver, in one sitting, a lethal dose of the rodentically-active substance before the rat becomes bait shy.

Some rodentically-active substances have poor chemical stability and, thus, have a poor shelf life. Stability may deteriorate further when such substances are exposed to environmental conditions. After such exposure, these substances typically have a relatively short half-life and, thus, become increasingly less active. By providing a highly palatable bait to the rodents, the rodents are encouraged to consume, in a single sitting, a sufficient amount of the bait to deliver a lethal dose of the active substance despite its decreasing activity.

It is clear, from the above, that the palatability of the bait is critical to ensure that the bait is effective in the control of rodent populations.

The major considerations in achieving a bait composition that is palatable to rodents comprise providing taste, aroma, texture and/or consistency that are attractive to the rodents.

In order to provide bait compositions having improved palatability compared to wax block baits, it has previously been proposed to formulate baits as pastes. DE 19837064A describes a rodenticide composition which comprises soya fat having a melting point of 32° C. EP-A-2497362 describes rodenticidal formulations in paste form which, inter alia, contain vegetable flour, one or more binding agents selected from refined and/or crude vegetable fats/oils having a melting point higher than 36-39° C. and paraffin waxes, and alkaline hydroxides as stabilizing agent. EP-B-1279334 discloses a combined bait with a rat-poisoning action comprising an active principal with a rodenticidal action and a baiting composition wherein the baiting composition comprises a component in paste form palatable to rodents comprising flour of a vegetable and/or animal origin associated with a component in solid form suitable for being gnawed by a rodent. WO-A-2004/098286 discloses a rodenticidal composition, in the form of a vegetable paste, comprising a fraction based on carbohydrates, prevalently of a vegetable origin, a fraction based on fatty matter, prevalently of a vegetable origin and at least one rodenticidally-active principal, characterised in that the fraction of fatty matter comprises a vegetable oil having an iodine index lower than 70.

Problems have been encountered with prior art paste baits. The choice of the fat used is crucial to the consistency, stability and palatability of the bait. For instance, if the fat melts, or separates out from the other components of the bait, under the environmental conditions in which the bait is used then the target rodents will not be attracted and will find the bait unpalatable. On the other hand, if the fat used is too hard under processing conditions then it becomes difficult to produce a homogeneous mixture of bait components. Furthermore, such a product, therefore, suffers from a reduced palatability.

In addition to the choice of fat, the ratio of fat to flour in the paste is also crucial for achieving the desired consistency in the processing operation and for achieving improved palatability of the product. A ratio that is too small increases the risk that the fat component separates out and/or is too dominant in the composition; both situations reducing the palatability of the composition to the target rodents. On the other hand, a ratio that is too high makes the production of the paste increasingly difficult and results in a product that, again, has reduced palatability.

We have found that existing paste baits, though having better palatability than conventional wax bait blocks, still do not have sufficiently high palatability to overcome the various problems identified above. It is the aim of the present invention to provide a rodenticidal soft bait block that has improved palatability for rodents. It is, further, the aim of the present invention to provide an extremely palatable bait formulation which overcomes difficulties arising in the production process. The invention, further, overcomes difficulties arising from the use of poorly stable rodenticidally-active substances.

Accordingly, the present invention provides a rodenticidal soft bait composition comprising a mixture, in the form of a paste, comprising vegetable flour, a fat which is not completely liquid at a temperature of 35° C. and at least one rodenticidally-active substance wherein the vegetable flour is present in the mixture in an amount of at least 60% by weight based on the total weight of the mixture and wherein the weight ratio of vegetable flour to fat is 4:1 to 8:1.

Typically, the soft bait composition of the invention comprises at least 60% by weight of the mixture in the form of a paste, as described above. Preferably, the bait composition comprises at least 80% by weight, and in particular at least 95% by weight, of the mixture described above. In another embodiment, the soft bait composition consists essentially of the mixture described above which is in the form of a paste.

The composition of the present invention comprises a mixture in the form of a paste. By the term "paste" used herein, we mean a soft, viscous material comprising a dispersion of fine particulate solids in fat which is capable of being moulded or shaped.

The composition of the invention comprises one or more vegetable flours. The vegetable flour will be a cereal flour or a non-cereal flour. Examples of suitable vegetable flours include cereal flours such as oat flour, wheat flour, rice flour and maize flour and non-cereal flours such as potato flour, peanut flour and soy flour. Preferably, the vegetable flour will be oat flour or a mixture of oat flour and wheat flour. Oat flour has a taste which is particularly attractive to rodents, especially rats. If a mixture of oat flour and wheat flour is used as the vegetable flour in the soft bait composition of the invention, the content of the wheat flour in the mixture will typically not exceed about 30% by weight based on the combined weight of the oat flour and wheat flour. Preferably, if the vegetable flour used consists of oat flour and wheat flour, the wheat flour will be used in an amount not exceeding 15% by weight based on the combined weight of the oat flour and wheat flour. The rodenticidal soft bait composition of the present invention contains the vegetable flour, as described above, in an amount which is at least 60% by weight based on the total weight of the composition. According to a preferred embodiment, the vegetable flour as described above is present in the composition of the invention in an amount not greater than 80% by weight based on the total weight of the composition. More preferably, the vegetable flour as described above, will be used in an amount of from 62 to 78% by weight based on the total weight of the composition.

The soft bait composition of the invention contains a fat which is not completely liquid at a temperature of 35° C., i.e. it is solid at normal room temperature (20° C.) but is not completely melted at 35° C. The fat may be an animal fat or a vegetable fat. Preferably, the fat is a vegetable fat and, more preferably, is refined palm oil. At a temperature of 35° C., refined palm oil contains a liquid (olein) fraction and a solid (stearin) fraction. Typically, the fat, preferably palm oil, content of the soft bait composition is not greater than 15% by weight based on the total weight of the composition. More preferably, the composition contains between 10 and 13% by weight of fat, preferably refined palm oil, based on the total weight of the composition. It is critical, in the present invention, to ensure that the weight ratio of vegetable flour to fat is within the range of 4:1 to 8:1. If the ratio is <4:1, there is an increasing tendency for fat to separate from the mixture, especially in warm environmental conditions, which results in a composition having reduced palatability to rodents. If the ratio is >8:1 then a mixture in the form of a paste, as defined herein, becomes increasingly more difficult to produce because of processing constraints. Preferably, the weight ratio of vegetable flour to fat is 5:1 to 7.5:1. According to a preferred embodiment, the composition of the invention contains a vegetable flour selected from oat flour, wheat flour and mixtures thereof and deodorized, refined palm oil wherein the weight ratio of the vegetable flour to palm oil is 6:1 to 7:1.

Preferably, the soft bait composition contains edible seeds. Examples of edible seeds that can be used in the soft bait composition of the invention will typically be ones that are less than 1 mm in length. Preferably, the edible seed is poppy seed since poppy seed is particularly palatable to rodents, especially rats. The amount of edible seed in the soft bait composition of the invention is typically in the range of from 0 to 1% by weight based on the total weight of the soft bait composition. According to a preferred embodiment, the soft bait composition contains about 0.5% by weight of poppy seed based on the total weight of the composition.

The soft bait composition of the invention contains at least one rodenticidally-active substance. The rodenticidally-active substance may be an anticoagulant rodenticide, a non-anticoagulant rodenticide or a natural or synthetic poison. Examples of suitable anticoagulant rodenticides include difenacoum, flocoumafen, brodifacoum, bromodiolone, diphacinone, difethialone, warfarin, sodium warfarin, coumatetralyl, chlorophacinone, coumachlor, coumafuryl and pindone. Examples of non-anticoagulant rodenticides include vitamin D, for instance cholecalciferol (vitamin D3) and ergocalciferol (vitamin D2) and norbormide. Other rodenticides that may be used in the present invention include natural poisons, such as strychnine and scilliroside, as well as synthetic poisons such as metal phosphides, for example zinc phosphide, sodium fluoroacetate and metal cyanides, for example sodium cyanide and α-chlorolose.

Microencapsulated forms of the rodenticidally-active substance may also be used in the composition of the present invention.

According to a preferred embodiment, the soft bait composition of the present invention contains a non-anticoagulant rodenticide and, more preferably, cholecalciferol. We have found that cholecalciferol is sufficiently toxic to rats and mice and is effective against anticoagulant-resistant rodents.

Typically, an anticoagulant rodenticide will be used in an amount in the range of from 0.001 to 0.05% by weight, preferably 0.001 to 0.025%, and more preferably 0.0025 to 0.025%, by weight based on the total weight of the bait composition. If the bait contains vitamin D as the rodenticidally-active substance, this will typically be used in an amount of 250-10000 ppm (0.025-1.0% by weight based on the total weight of the bait). The actual amount used will, of course, depend on the identity of the rodenticidally-active substance used and on the target pest.

According to a preferred embodiment, a soft bait composition of the present invention which is particularly palatable to rodents, especially to rats, consists of a mixture, in the form of a paste, comprising oat flour, refined palm oil and, as rodenticidally-active substance, cholecalciferol wherein the oat flour is present in an amount of at least 60% by weight based on the total weight of the composition and wherein the weight ratio of oat flour to refined palm oil is from 5:1 to 6:1.

According to a more preferred embodiment, the soft bait composition comprises about 0.075% by weight of cholecalciferol, about 10.0% by weight of wheat flour, about 11.5% by weight of refined, deodorised palm oil and about 64% by weight of oat flour, all percentages being based on the total weight of the soft bait composition.

The soft bait composition of the present invention may, advantageously, also contain one or more components such as sweetening agents, vegetable oil, additional food components, pigments or dyes, flavouring agents, preservatives, antioxidants, fungistats and taste deterrents. Such additional components are well known to the person skilled in the art.

Preferably, the soft bait composition contains a sweetening agent. Typically, the sweetening agent is sucrose, preferably icing sugar. According to an embodiment, the soft bait composition contains from 10 to 15% by weight, preferably about 10% by weight, of sucrose, preferably icing sugar, based on the total weight of the soft bait composition.

Although palm oil and icing sugar in the soft bait composition provide flavours which are very attractive to rodents, it may further be desired to include one or more additional agents which provide extra flavours and/or aromas to the soft bait composition to increase yet further the palatability of the composition.

It is conventional, in the art of rodenticides, to include one or more substances which act as a deterrent to humans. Such substances typically provide a flavour which is repellent to humans. Typical of such substances are bittering substances which give a bait an unpleasant taste noticeable to humans. An example of such a taste deterrent is denatonium benzoate. Such deterrent substances may be included in a total amount which is typically about 0.001% by weight based on the total weight of the soft bait composition.

The soft bait composition will typically be coloured, by the incorporation of a colourant, e.g. a dye or pigment, to aid identification. Typically, a colourant will be present in an amount of about 0.002% by weight based on the total weight of the composition.

The rodenticidal soft bait composition of the invention may be manufactured by a process which comprises the steps:
(a) preparing a premix of one or more rodenticidally-active substance in a solvent or liquid carrier;
(b) preparing a mixture of the vegetable flour and the fat and any optional sweetening agent, food components, dyes or pigments;
(c) blending the premix prepared in step (a) with the mixture prepared in step (b) to give a substantially homogeneous blend.

According to step (a) of the process, the one or more rodenticidally-active substance is mixed with a solvent or a liquid carrier. The solvent or liquid carrier used will be one that enables a solution, dispersion or emulsion containing the rodenticidally-active substance to be prepared. Obviously, the use of any solvent or liquid carrier which has a flavour and/or aroma that detracts from the flavour and/or aroma of the final formulation of the soft bait composition is not preferred. Typical solvents and/or liquid carriers for the rodenticidally-active substance include vegetable oils. A preferred vegetable oil is maize oil. The amount of solvent and/or liquid carrier used will be such that the final soft bait composition typically contains from 1 to 4% by weight of solvent and/or liquid carrier based on the total weight of the soft bait composition. According to a preferred embodiment, maize oil is used as the solvent wherein the proportion of maize oil is such that the final soft bait composition contains from 1 to 3.0% by weight of maize oil based on the total weight of the soft bait composition. It is known that some rodenticidally-active substances, for instance ergocalciferol, suffer from poor chemical stability particularly in the presence of moisture. We have found that stability of such substances is greatly enhanced when they are used in vegetable oil-based formulations.

The mixture prepared in step (b) of the process contains the vegetable flour and fat and any optional extra food ingredients, sweetener, colouring matter etc. of the desired soft bait composition. The mixture can be prepared using any conventional mixing or blending apparatus.

After the premix of step (a) and the mixture of step (b) have been prepared, the premix of step (a) is added to the mixture of step (b) and the combination of ingredients is subjected to mixing so that a substantially homogeneous blend is obtained. If it is also desired to incorporate a human taste deterrent (e.g. denatonium benzoate) into the composition, an additive premix comprising a solution of the taste deterrent in a suitable solvent is prepared and this additive premix will conveniently be blended into the mixture obtained in step (b) above before the active premix of step (a) is added. Suitable solvents for denatonium benzoate for use in the preparation of the additive premix include lower alkylene glycols, for example monopropylene glycol. It may further be desired to include a fungistat, for example orthophenyl phenol, in the additive premix.

The rodenticidal soft bait composition of the invention will typically be packaged or wrapped for use. For instance, the composition may be packaged into single dosage packages, such as paper sachets which, in use, may be positioned in suitable locations, for example in bait boxes, in the vicinity of known or suspected rodent activity.

EXAMPLES

Three different soft bait compositions according to the present invention were prepared having the formulations shown in Table 1 below. Each formulation was prepared by initially forming a premix of cholecalciferol and maize oil. A separate additive premix of denatonium benzoate and monopropylene glycol was prepared and this additive premix was blended with the vegetable flours, icing sugar, refined palm oil, poppy seed, dye and silica. The cholecalciferol/maize oil premix was then blended into the mixture of the other components of the formulation to produce a homogeneous mixture. The mixture obtained was then packaged into single dosage paper sachets.

TABLE 1

|  | Example 1 | Example 2 | Example 3 |
| --- | --- | --- | --- |
| Cholecalciferol | 750 ppm | 750 ppm | 750 ppm |
| Maize oil | 2.5% | 2.5% | 2.5% |
| Denatonium benzoate | 0.001% | 0.001% | 0.001% |
| Monopropylene glycol | 1.0% | 1.0% | 1.0% |
| Wheat flour | 9.422% | 10.922% | 7.922% |
| Oat flour | 60% | 63% | 60% |
| Icing sugar | 10% | 10% | 12% |
| Refined Palm Oil | 15% | 12% | 15% |
| Poppy seed | 0.5% | 0.5% | 0.5% |
| Dye | 0.002% | 0.002% | 0.002% |
| Silica | 1.5% | 0 | 1.0% |

Each of the sacheted soft bait compositions prepared above was subjected to palatability testing using male Wistar Rats. Commercially-available products were also subjected to palatability testing under the same conditions. The commercially-available products tested were:
Rodilon (Registered Trade Mark) Soft Block
(active—difethialone)—Bayer
Muskil (Registered Trade Mark) Pasta
(actives—difenacoum and bromadiolone)—Zapi
Cholecalciferol wax block (Bell Labs)
Test Procedure The test bait and an alternative control (containing no active substance) were offered to each of five male Wistar Rats. The alternative control used in the test was LabDiet (Registered Trade Mark) EURodent Diet 22% 5LFS from PMI Nutrition International. The ingredient composition of this diet is:

| cereal products (corn, wheat, wheat middlings) | 58.2% |
|---|---|
| vegetable proteins (dehulled soybean meal, dehydrated alfalfa, dried beet pulp, dried brewers yeast) | 37.2% |
| energy sources (soybean oil) | 1.75% |
| supplementation (vitamins, major minerals, trace minerals, amino acids) | 2.85% |

The total test bait and control diet takes for all five animals were summed and the palatability ratio for each test bait was calculated as follows:

$$\text{Palatability Ratio (group of five animals)} = \frac{\text{Total test bait take (g)}}{\text{Total control diet take (g)}}$$

Thus, a palatability ratio of >1.0 indicates that the test bait was more palatable to the rats than the control diet whereas a palatability ratio of 1.0 indicates that the test bait and the control diet were equally palatable. The palatability ratios obtained for all test baits are shown in Table 2 below.

TABLE 2

| Test bait | Palatability ratio |
|---|---|
| Ex 1 | 7.9 |
| Ex 2 | 6.1 |
| Ex 3 | 4.56 |
| Rodilon ® Soft Block | 1.2 |
| Muskil ® Pasta | 1 |
| Cholecalciferol wax block (Bell) | 0.9 |

The results reported in Table 2 show that soft bait compositions according to the present invention were found to be significantly more palatable to the test rats compared to other products tested.

The invention claimed is:

1. A rodenticidal soft bait composition comprising a mixture, in the form of a paste, comprising vegetable flour, a fat which is not completely liquid at a temperature of 35° C. and at least one rodenticidally-active substance wherein the vegetable flour is present in the mixture in an amount of at least 60% by weight based on the total weight of the mixture and wherein the weight ratio of vegetable flour to fat is 4:1 to 8:1.

2. The composition according to claim 1, wherein the vegetable flour is present in the mixture in an amount of not greater than 80% by weight based on the total weight of the mixture.

3. The composition according to claim 2, wherein the vegetable flour is present in the mixture in an amount of 62 to 78% by weight based on the total weight of the mixture.

4. The composition according to claim 1, wherein the vegetable flour is selected from oat flour, wheat flour, rice flour, maize flour and mixtures of two or more of these.

5. The composition according to claim 4, wherein the vegetable flour is oat flour.

6. The composition according to claim 1, wherein the fat is refined palm oil.

7. The composition according to claim 1, wherein the weight ratio of vegetable flour to fat is 5:1 to 7.5:1.

8. The composition according to claim 6, wherein the vegetable flour comprises oat flour and wherein the ratio of vegetable flour to fat is 5:1 to 6:1.

9. The composition according to claim 1, wherein the rodenticidally-active substance is selected from difenacoum, flocoumafen, brodifacoum, bromodiolone, diphacinone, difethialone, warfarin, sodium warfarin, coumatetralyl, chlorophacinone, coumachlor, coumafuryl and pindone.

10. The composition according to claim 1, wherein the rodenticidally-active substance is cholecalciferol or ergocalciferol.

11. The composition according to claim 10, wherein the rodenticidally-active substance is cholecalciferol.

12. The composition according to claim 11, wherein the cholecalciferol is present in the composition in an amount of from 250 to 10000 ppm.

13. A method for preparing the composition of claim 1, which comprises the steps:
  (a) preparing a premix of one or more rodenticidally-active substances in a solvent or liquid carrier;
  (b) preparing a mixture of the vegetable flour and the fat; and
  (c) blending the premix obtained in step (a) with the mixture obtained in step (b) to give a substantially homogeneous blend,
  thereby obtaining a composition according to claim 1.

14. The method of claim 13, wherein the vegetable flour is present in the mixture in an amount of not greater than 80% by weight based on the total weight of the mixture.

15. The method of claim 14, wherein the vegetable flour is present in the mixture in an amount of 62 to 78% by weight based on the total weight of the mixture.

16. The method of claim 13, wherein the vegetable flour is selected from oat flour, wheat flour, rice flour, maize flour and mixtures of two or more of these.

17. The method of claim 16, wherein the vegetable flour is oat flour.

18. The method of claim 13, wherein the fat is refined palm oil.

19. The method of claim 13, wherein the weight ratio of vegetable flour to fat is 5:1 to 7.5:1.

20. The method of claim 19, wherein the vegetable flour comprises oat flour and wherein the ratio of vegetable flour to fat is 5:1 to 6:1.

21. The method of claim 12, wherein the rodenticidally-active substance is selected from difenacoum, flocoumafen, brodifacoum, bromodiolone, diphacinone, difethialone, warfarin, sodium warfarin, coumatetralyl, chlorophacinone, coumachlor, coumafuryl and pindone.

22. The method of claim 13, wherein the rodenticidally-active substance is cholecalciferol or ergocalciferol.

23. The method of claim 22, wherein the rodenticidally-active substance is cholecalciferol.

24. The method of claim 23, wherein the cholecalciferol is present in the composition in an amount of from 250 to 10000 ppm.

25. The composition of claim 1, wherein the bait composition further contains edible seeds.

26. The composition of claim 25, wherein the edible seeds are less than 1 mm in length.

27. The composition of claim 25, wherein the edible seeds are poppy seeds.

* * * * *